United States Patent [19]

Gaudet et al.

[11] Patent Number: 4,981,480

[45] Date of Patent: Jan. 1, 1991

[54] ADJUSTABLE CHILD GARMENT

[76] Inventors: Melody L. Gaudet, 1045 Quadling Ave., Coquitlam, B.C., Canada, V3K 2B1; Annette C. Beauregard, 3970 Cedar Dr., Port Coquitlam, B.C., Canada, V3B 3E5; Teresa L. Topping, 1025 Quadling Ave., Coquitlam, B.C., Canada, V3K 2A9

[21] Appl. No.: 531,216

[22] Filed: May 31, 1990

[51] Int. Cl.⁵ ............................................. A61F 13/15
[52] U.S. Cl. ................................. 604/386; 604/385.1; 2/221
[58] Field of Search ................. 604/385.1, 386; 2/221, 2/235, 236, 400, 402, 406, 408

[56] References Cited

U.S. PATENT DOCUMENTS

| | | | |
|---|---|---|---|
| 4,338,938 | 7/1982 | Seavitt | 128/248 |
| 4,475,912 | 10/1984 | Coates | 604/385 |
| 4,568,342 | 2/1986 | Davis | 604/391 |
| 4,704,117 | 11/1987 | Mitchell | 604/391 |
| 4,728,326 | 3/1988 | Gilles | 604/391 |
| 4,773,906 | 9/1988 | Krushel | 604/391 |
| 4,801,298 | 1/1989 | Sorenson et al. | 604/384 |

Primary Examiner—Randall L. Green
Assistant Examiner—Gina M. Gualtieri
Attorney, Agent, or Firm—Townsend and Townsend

[57] ABSTRACT

An adjustable child garment, specifically a diaper or a diaper wrap, can be used by a child from birth until diapers are no longer required. The garment comprises a substantially rectangular panel having a back with back side tabs extending from the top on each side, the back side tabs each having a first hook strip pad on the inside surface, the panel having a front with front side tabs extending from the top on each side, a loop strip ribbon extending across the top on the outside of the front of the panel from one front side tab to the other, the first hook strip pads detachably engageable with the loop strip ribbon. Elastic is sewn along the back of the panel and along each side of the panel between the back side tabs and the front side tabs. The outside of the front of the panel has a second hook strip pad below the loop strip ribbon and at least one loop strip pad, spaced below the second hook strip pad such that the top of the front of the panel can be folded in an S-configuration with the second hook strip pad engageable with the loop stripped to reduce the size of the garment for a smaller child.

11 Claims, 3 Drawing Sheets

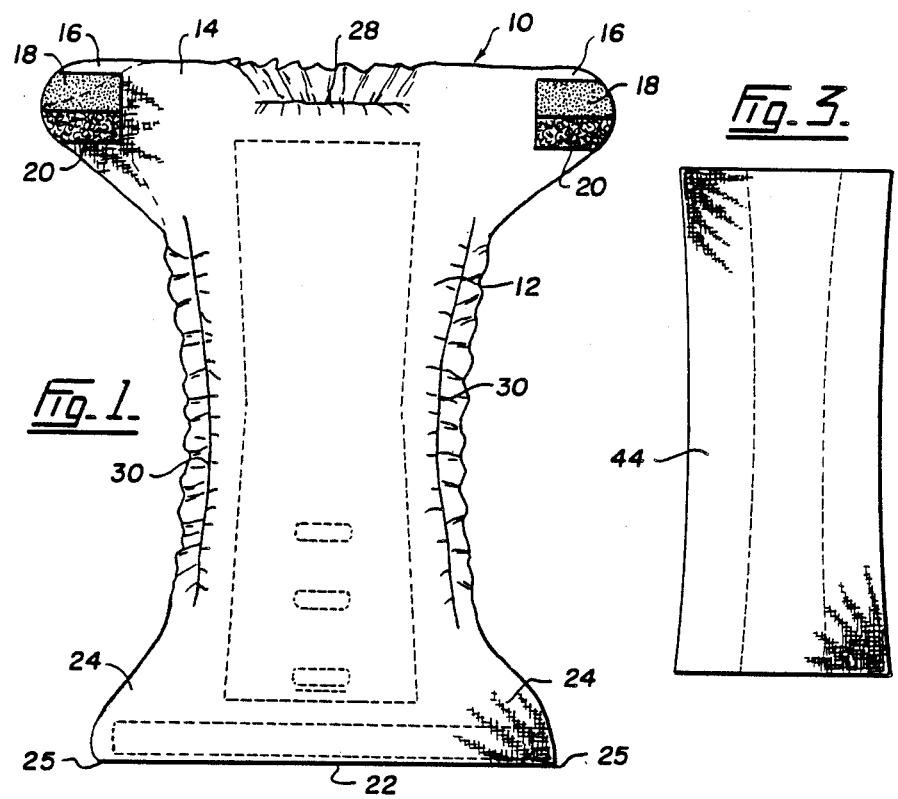
Fig. 3.
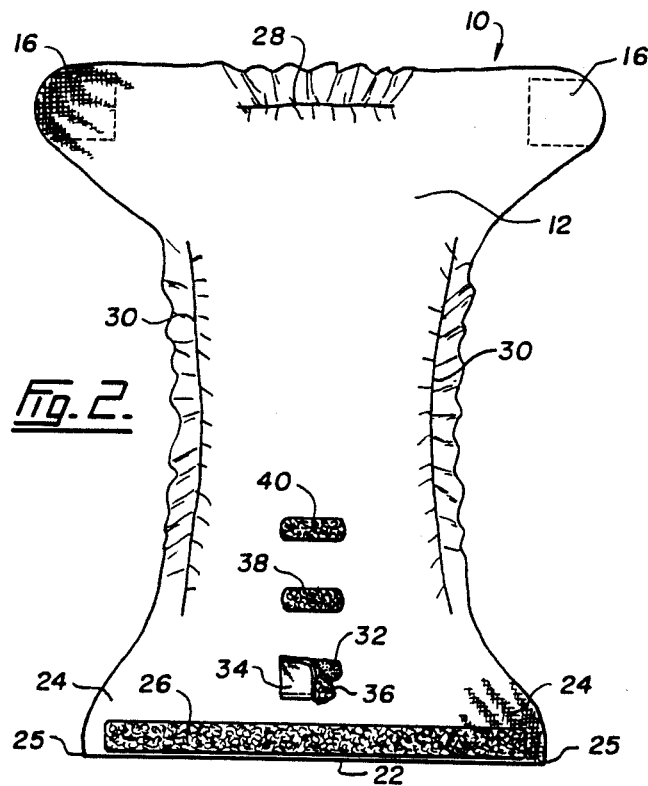

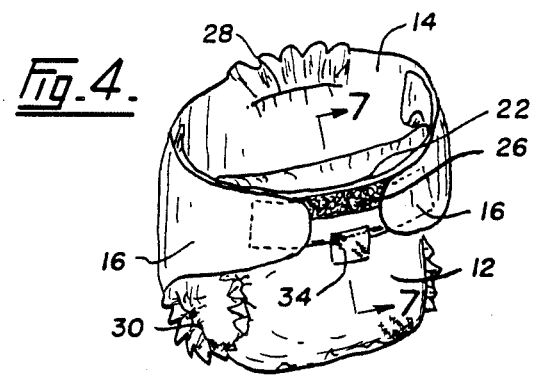
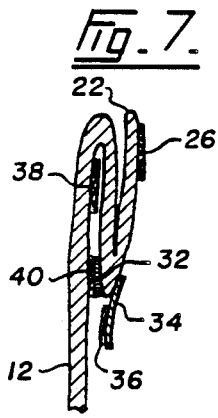
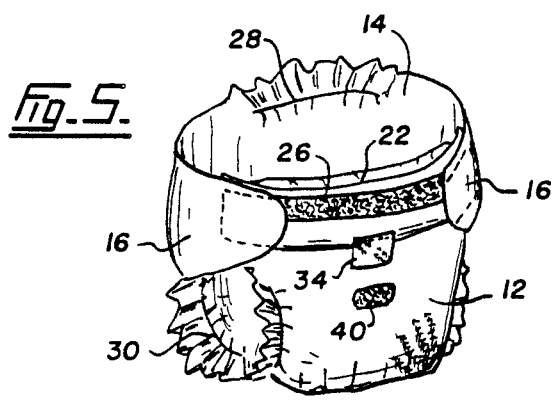
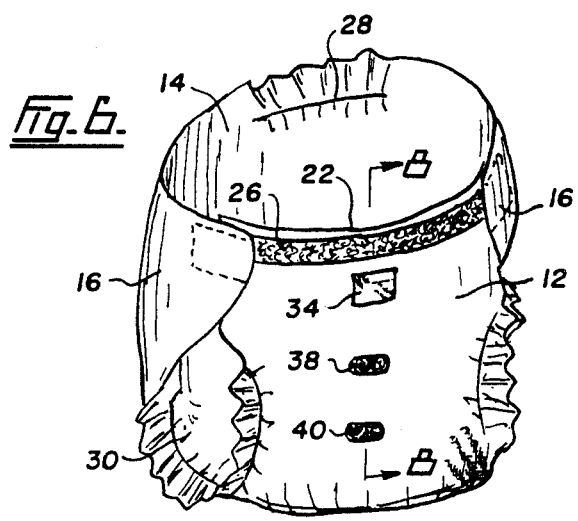
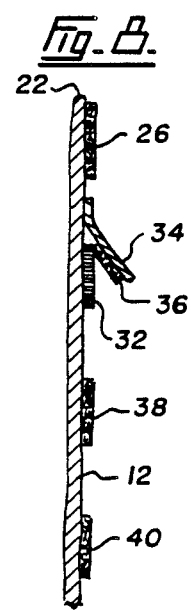

4,981,480

1

ADJUSTABLE CHILD GARMENT

The present invention relates to an adjustable child garment such as a reusable diaper or a diaper wrap that may be used for infants from birth until they no longer require diapers.

Cloth diapers were initially made having a rectangular shape and were folded and pinned to a child. The diapers were often covered by rubber pants, particular for heavy wetters.

Cloth diapers then were at least partially replaced in some circles by disposable diapers which could be thrown away after use, and thus avoided the necessity of washing diapers. However today it is considered that the use of disposable diapers increases the problem of garbage disposal since disposable diapers do not easily degrade. Instead they fill garbage sites and this is environmentally unacceptable.

There is therefore a requirement for a reusable diaper and preferably one that can be used by a child from birth until a diaper is no longer required. A long lasting adjustable diaper reduces the cost of diaper replacement when infants grow. Furthermore, such diapers may be provided by diaper services and in this day and age can be made to fit a child and attach by means of hook strips and loop strips, or snaps rather than safety pins as in the old rectangular shaped diapers. Furthermore there is a requirement for a diaper wrap which is of the same design as the diaper and made of waterproof material which can be used over the top of a diaper. The diaper wrap is also adjustable for different sizes of children.

The present invention provides an adjustable child garment suitable for a diaper and a diaper wrap, the garment comprising a substantially rectangular panel having a back with back side tabs extending from the top on each side, the back side tabs each having a first hook strip pad on the inside surface, the panel having a front with front side tabs extending from the top on each side, a loop strip ribbon extending across the top on the outside of the front of the panel from one front side tab to the other, the first hook strip pads detachably engageable with the loop strip ribbon; elastic sewn along the back of the panel, elastic sewn along the back of the panel, and elastic sewn along each side of the panel between the back side tabs and the front side tabs, and the outside of the front of the panel having a second hook strip pad below the loop strip ribbon and at least one loop strip pad, spaced below the second hook strip pad such that the top of the front of the panel can be folded in an S-configuration with the second hook strip pad engageable with the loop strip pad to reduce the size of the garment for a smaller child.

In one embodiment the garment is a diaper wrap and in another embodiment the garment is a diaper.

The present invention also provides an adjustable, reusable diaper comprising a substantially rectangular panel formed of double layers of soft woven material, the panel having a back with back side tabs extending from the top on each side, the back side tabs each having a first hook strip pad on the inside surface; the panel having a front with front side tabs extending from the top on each side, a loop strip ribbon extending across the top on the outside of the front of the panel from one front side tab to the other, the first hook strip pads detachably engageable with the loop strip ribbon; elastic sewn along the back of the panel, and elastic sewn along each side of the panel between the back side tabs

2 and the front side tabs; absorbent material sewn between the double layers of the panel within the elastic and the loop strip ribbon, and the outside of the front of the panel having a second hook strip pad below the loop strip ribbon and at least one loop strip pad spaced below the hook strip pad such that the top of the front of the panel can be folded in an S-configuration with the second hook strip pad engageable with the loop strip pad to reduce the size of the diaper for a smaller child.

In a still further embodiment the two first hook strip pads on the back side tabs are replaced with at least one snap fastener, and the loop strip ribbon extending across the top on the outside of the front of the panel is replaced with a row of mating snap fasteners to mate with the snap fasteners on the back side tabs. Furthermore, the second hook strip pad below the row of mating snap fasteners is replaced with at least one snap fastener, and at least one loop strip pad below the second hook strip pad is replaced with at least one mating snap fastener. Thus the snap fastener replaces the hook strips and loop strips, but the garment is otherwise similar.

In drawings which illustrate embodiments of the invention,

FIG. 1 is an inside plan view of a diaper according to one embodiment of the invention in the open position.

FIG. 2 is an outside plan view of the diaper shown in FIG. 1.

FIG. 3 is a plan view of a separate absorbent panel for use with the diaper shown in FIGS. 1 and 2.

FIG. 4 is an isometric view of a diaper folded over to its smallest size for a small infant.

FIG. 5 is an isometric view of the diaper shown in FIG. 4 folded to its intermediate size.

FIG. 6 is an isometric view of the diaper shown in FIG. 4 opened out to its maximum size.

FIG. 7 is a sectional view taken through line 7—7 of FIG. 4.

FIG. 8 is a sectional view taken through line 8—8 of FIG. 6.

Figure 9:
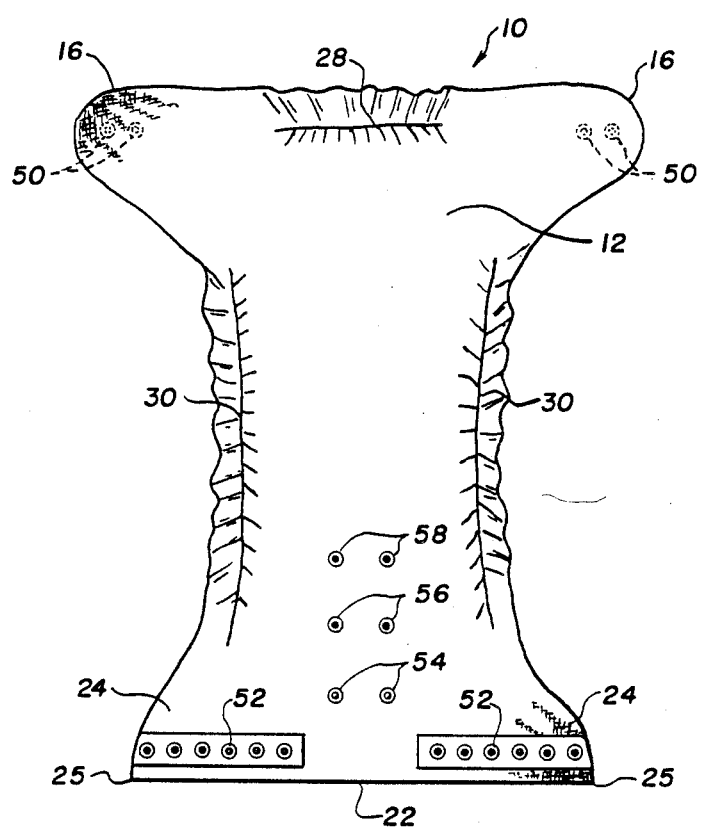
FIG. 9 is an outside view of a diaper according to another embodiment of the invention wherein the hook and loop pads are replaced with snap fasteners.

The drawings all illustrate an adjustable child diaper, however, whereas a diaper is shown here it will be apparent that the shape could be applied to a diaper wrap made of an elastomeric material such as that sold under the trade mark LYCRA, or a waterproof material for purposes of placing over an ordinary diaper or a different type of diaper particularly in situations where the child is a heavy wetter.

The diaper 10 shown in FIGS. 1 and 2 is generally formed of a rectangular panel 12 made of double layers of soft woven material such as felt or flannelette, with an intermediate absorbent layer of woven or nonwoven material therebetween. The material may be a batting of rayon, polyester, cotton or a mixture of these materials which have high absorbency. The back top edge 14 of the panel 12 extends on either side to back side tabs 16 which each have a hook strip pad 18 attached at the top on the inside of the back side tabs 16. The hook strip pad 18 is part of a hook and loop attachment arrangement of the type well known and sometimes referred to under the trade mark Velcro. Directly beneath the hook strip pads 18 are two loop strip pads 20, substantially the same size as the hook strip pads 18. The purpose of these loop strip pads 20 is to fold over and engage the hook strip pads 18 when the diaper 10 is being washed. Thus the hook strip pads 18 are not able to stick to other garments in a washing machine. It is found that if hook strip pads are washed without being engaged with a loop strip pad, or some other type of protection, then other garments in the batch of washing tends to stick to the pads.

The panel 10 has a front top edge 22 opposite the back top edge 14 with front side tabs 24 on each side extending out beyond the generally rectangular configuration of the panel 12. The front side tabs 24 have corners 25 at each end of the front top edge 22. The corners 25 are sharper than those between the back side tabs 16 joining to the back top edge 14. A loop strip ribbon 26 extends on the outside of the panel 12 across the front top edge 22 from one front side tab 24 to the other front side tab 24. The loop strip ribbon 26 can be engaged at different locations by the hook strip pads 16 when the diaper is folded into a garment on a child. The hook strip pads 18 are on the inside of the back side tabs 16 and the loop strip ribbon 26 is on the outside of the panel 12, this engagement between the hooks and loops occurs when the garment is folded.

Elastic stitching 28 is shown along the back top edge 14 of the panel 12 between the back side tabs 16 and elastic stitching 30 is also shown on each side of the panel between the back side tabs 16 and the front side tabs 24.

On the front of the outside of the panel 12, directly beneath the loop strip ribbon 26, is a second hook strip pad 32 in the approximate center of the panel 12. A cover flap 34, with a loop strip pad 36 on the inside thereof, is sewn at its top directly above the second hook strip pad 32, thus when the diaper is to be washed the cover flap 34 is down with the loop strip pad 36 engaging with the second hook strip pad 32.

Two further loop strip pads 38 and 40 are positioned on the outside of the panel 12 in the approximate center spaced down from the second hook strip pad 32.

FIG. 3 illustrates a separate absorbent panel 44 which is formed of two layers of soft woven material, such as felt or flannelette, with an absorbent layer, preferably a batting woven or nonwoven rayon, or polyester, cotton or other mixtures thereof, therebetween. The separate absorbent panel 44 is used for children who are heavy wetters, and is placed on the inside of the diaper as shown in the dotted line in FIG. 1 before the diaper is fitted to the child. The separate absorbent panel 44 may not be necessary in the day, but may be used for night wear. The use is dependent upon the particular child.

FIG. 4 illustrates the diaper shown in FIGS. 1 and 2 folded to suit a newborn infant. FIG. 5 represents the next size of infant and FIG. 6 represents the largest child size. When the diaper is folded to fit a newborn child, as shown as FIG. 4, the cover flap 34 is lifted off the second hook strip pad 32 and the whole front of the panel is folded in an S-configuration so that the second hook strip pad 32 engages with the lowest loop strip pad 40 as shown in.FIG. 7. Thus the size of the diaper is reduced by the S-configuration fold. In this form the diaper is placed on the child and the back side tabs 16 are brought forward so the hook strip pads 18 engage the loop strip ribbon 26 on the top front edge 22 of the panel 12. The loop strip ribbon 26 allows for different dimensions for the waist of the child as the hooks engage in the loops wherever contact is made. The elastic side stitching 30 mold to the child's legs and the back elastic stitching 28 allows movement for the child to stretch. This helps to retain moisture within the diaper and restricts leakage.

As the child grows, the next adjustment of the diaper occurs when the S-configuration is not so pronounced and the second hook strip pad 32 engages with the upper loop strip pad 38. The waist of the child has obviously grown at this time and therefore the back side tabs 16 do not extend as far around on the loop strip ribbon 20 as in the configuration shown in FIG. 4.

When the child is walking, the largest size of diaper is generally required such as that shown in FIG. 6. In this configuration no folds occur in the front of the panel as shown in FIG. 8. The back side tabs 16 are brought forward and the hook strip pads 18 engage on the outer edges of the loop strip ribbon 26. The cover flap 34 is pushed down so that the second hook strip pad 32 is protected by the loop strip pad 36, and therefore does not stick to other clothing worn by the child. As can be seen, the loop strip pads 38 and 40 are visible on the front of the diaper but these do not stick to other garments.

Another embodiment of the garment, either a diaper or a diaper wrap, is shown in FIG. 9 wherein the hook strip pads 18 of FIG. 1 are replaced with two male snap fasteners 50 on the inside of the back side tabs 16. The loop strip ribbon 26 shown in FIG. 2 is replaced with two rows of female snap fasteners 52. This permits a variation in the child's waist as only one fastener 50 need engage with one female fastener 52.

The hook strip pads 32 and loop strip pads 38 and 40 shown in FIG. 2 are replaced with two male snap fasteners 54 at the top and two female fasteners 56 in a first row and the two female fasteners 58 below. The snap fasteners replace the hook and loop strips but the garment can be folded in the S-configuration in the same way as shown in FIG. 7.

When the garment is made as a diaper wrap, that is to say a garment to surround a diaper, it is made of waterproof material but has substantially the same form as that described herein and shown in the drawings with the exception that there are not multiple layers as in the case of a diaper. The wrap is foldable in the front for the three sizes as shown in FIGS. 4, 5 and 6. By having the separate absorbent panel 44 as shown in FIG. 3, one is able to wash the panel 44 separately and this is particularly useful as the bulk is reduced and there is less drying time needed for drying the diaper and the absorbent panel 44.

The diaper or diaper wrap may be reused, that is to say the so called back placed at the front of a child. The front side tabs cannot then be pulled free by a child. Placing the diaper back to front is generally only applicable when the diaper is in the largest configuration with no folds in the front panel. Whence as the diaper has been described as for a child from birth to when diapers are not required, the design can be used in larger sizes for incontinent adolescents or adults.

Various changes may be made to the embodiments shown and described herein without departing from the scope of the present invention which is limited only by the following claims.

The embodiments of the present invention in which an exclusive property or privilege is claimed are defined as follows:

1. An adjustable child garment suitable for a diaper and a diaper wrap, the garment comprising:
    a substantially rectangular panel having a back with back side tabs extending from a top portion on each side, the back side tabs each having a first hook strip pad on a inside surface, the panel having a front with front side tabs extending from the top on each side, a loop strip ribbon extending across a top edge on outside of the front of the panel from one front side tab to the other, the first hook strip pads detachably engageable with the loop strip ribbon;

elastic sewn along the back of the panel, and elastic sewn along each side of the panel between the back side tabs and the front side tabs, and the outside of the front of the panel having a second hook strip pad below the loop strip ribbon and at least one loop strip pad, spaced below the second hook strip pad such that the top portion of the front of the panel can be folded in an S-configuration with the second hook strip pad engageable with one of said at least one loop strip pads to reduce the size of the garment for a smaller child.

2. The adjustable child garment according to claim 1 wherein the garment is a diaper wrap to fit over a diaper worn by a child, the diaper wrap being made of a waterproof material.

3. An adjustable, reusable diaper comprising:

a substantially rectangular panel formed of double layers of soft woven material, the panel having a back with back side tabs extending from a top portion on each side, the back side tabs each having a first hook strip pad on an inside surface;

the panel having a front with front side tabs extending from a top portion on each side, a loop strip ribbon extending across a top on the outside of the front of the panel from one front side tab to the other, the first hook strip pads detachably engageable with the loop strip ribbon;

elastic sewn along the back of the panel, and elastic sewn along each side of the panel between the back side tabs and the front side tabs;

absorbent material sewn between the double layers of the panel within the elastic and the loop strip ribbon, and the outside of the front of the panel having a second hook strip pad below the loop strip ribbon and at least one loop strip pad spaced below the second hook strip pad such that the top portion of the front of the panel can be folded in an S-configuration with the second hook strip pad engageable with one of the at least one loop strip pads to reduce the size of the diaper for a smaller child.

4. The diaper according to claim 3 wherein a cover flap is provided sewn to the outside of the front of the panel above the second hook strip pad, the cover flap having a loop strip portion on an inside to engage the second hook strip pad when the panel is not folded into an S-configuration.

5. The diaper according to claim 4 including additional loop strip pads attached on the inside surface of the back side tabs adjacent the first hook strip pads, the additional loop strip pads adapted to be folded over to engage the first hook strip pads when the diaper is washed.

6. The diaper according to claim 3 including a separate absorbent member formed of two layers of soft woven material with absorbent material in between, the separate member sized to fit when the panel is not folded in an S-configuration, and being of substantially the same size as the absorbent material between the double layers of the panel.

7. The diaper according to claim 3 wherein the soft woven material is felt or flannelette.

8. The diaper according to claim 3 wherein the absorbent material is woven or nonwoven batting of rayon, polyester, cotton or mixtures thereof.

9. The diaper according to claim 3 wherein two loop strip pads are spaced below the second hook strip pad thus allowing the diaper to have three adjustments for a growing child.

10. An adjustable child garment suitable for a diaper and a diaper wrap, the garment comprising:

a substantially rectangular panel having a back with back side tabs each having at least one snap fastener on an inside surface, the panel having a front with front side tabs extending from a top portion on each side, a row of mating snap fasteners to mate with the snap fasteners on the back side tabs, the row of mating snap fasteners extending across a top portion on an outside of the front of the panel from one front side tab to the other, elastic sewn along the back of the panel, and elastic sewn along each side of the panel between the back side tabs and the front side tabs, and the outside of the front of the panel having a further snap fastener below the row of mating snap fasteners and at least one further mating snap fastener, spaced below the further snap fastener such that the top portion of the front of the panel can be folded in an S-configuration with the further snap fastener engageable with one of the at least one further mating snap fasteners to reduce the size of the garment for a smaller child.

11. The adjustable child garment according to claim 10 wherein two snap fasteners are provided on the inside surface of each of the back side tabs, and wherein a row of two further snap fasteners is provided below the row of mating snap fasteners and two rows containing two further mating snap fasteners spaced below the two further snap fasteners to provide two reductions in size of the garment.

* * * * *